United States Patent [19]

Heider et al.

[11] 4,379,788
[45] Apr. 12, 1983

[54] 2-PHENYL-PYRIMIDONES

[75] Inventors: Joachim Heider, Warthausen; Volkhard Austel, Biberach; Wolfgang Eberlein, Biberach; Rudolf Kadatz, Biberach, all of Fed. Rep. of Germany; Christian Lillie, Vienna, Austria

[73] Assignee: Dr. Karl Thomae Gesellschaft mit beschränkter Haftung, Biberach an der Riss, Fed. Rep. of Germany

[21] Appl. No.: 327,348

[22] Filed: Dec. 4, 1981

[30] Foreign Application Priority Data

Dec. 12, 1980 [DE] Fed. Rep. of Germany ....... 3046871
Apr. 16, 1981 [DE] Fed. Rep. of Germany ....... 3115447

[51] Int. Cl.³ .................. A61K 31/505; C07D 239/91
[52] U.S. Cl. .................................... 424/251; 544/279; 544/289
[58] Field of Search ................. 544/279, 289; 424/251

[56] References Cited

FOREIGN PATENT DOCUMENTS 2348111 5/1974 Fed. Rep. of Germany ...... 544/279

*Primary Examiner*—Mary C. Lee
*Assistant Examiner*—James H. Turnipseed
*Attorney, Agent, or Firm*—Hammond & Littell, Weissenberger & Muserlian

[57] ABSTRACT

Compounds of the formula

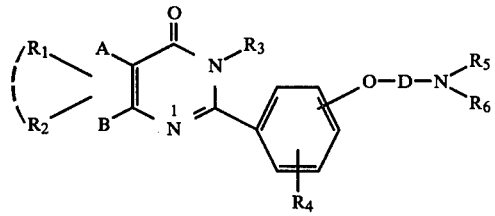

wherein
A and B, together with each other and the respective carbon atoms to which they are attached, form a phenyl or pyridine ring;
$R_1$ is hydrogen, halogen, amino, nitro, alkyl of 1 to 3 carbon atoms or alkoxy of 1 to 3 carbon atoms;
$R_2$ is hydrogen or alkoxy of 1 to 3 carbon atoms;
D is alkylene of 3 to 4 carbon atoms or hydroxy(alkylene of 3 to 4 carbon atoms);
$R_3$ and $R_5$, which may be identical to or different from each other, are each hydrogen or alkyl of 1 to 3 carbon atoms;
$R_4$ is hydrogen or alkoxy of 1 to 3 carbon atoms; and
$R_6$ is straight or branched alkyl of 1 to 6 carbon atoms or —E—$R_7$;
where E is straight alkylene of 2 to 4 carbon atoms or hydroxy-substituted straight alkylene of 2 to 4 carbon atoms, and
$R_7$ is

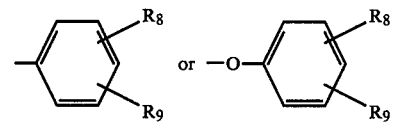

where $R_8$ and $R_9$ are each hydrogen, alkyl of 1 to 3 carbon atoms or alkoxy of 1 to 3 carbon atoms;
and non-toxic, pharmacologically acceptable acid addition salts thereof formed with inorganic or organic acids; the compounds as well as their salts are useful as hypotensives, antiarrhythmics and β-receptor-blockers.

9 Claims, No Drawings

2-PHENYL-PYRIMIDONES

This invention relates to novel 2-phenyl-pyrimidones and acid addition salts thereof, to methods of preparing these compounds, to pharmaceutical compositions containing them as active ingredients, and to methods of using them as hypotensives, antiarrhythmics and $\beta$-receptor blocking agents.

More particularly, the present invention relates to a novel class of compounds represented by the formula

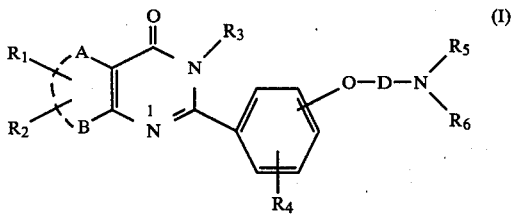

wherein

A and B, together with each other and the respective carbon atoms to which they are attached, form a phenyl or pyridine ring;

$R_1$ is hydrogen, halogen, amino, nitro, alkyl of 1 to 3 carbon atoms or alkoxy of 1 to 3 carbon atoms;

$R_2$ is hydrogen or alkoxy of 1 to 3 carbon atoms;

D is alkylene of 3 to 4 carbon atoms or hydroxy (alkylene of 3 to 4 carbon atoms);

$R_3$ and $R_5$, which may be identical to or different from each other, are each hydrogen or alkyl of 1 to 3 carbon atoms;

$R_4$ is hydrogen or alkoxy of 1 to 3 carbon atoms; and $R_6$ is straight or branched alkyl of 1 to 6 carbon atoms or —E—$R_7$;

where E is straight alkylene of 2 to 4 carbon atoms or hydroxy-substituted straight alkylene of 2 to 4 carbon atoms, and $R_7$ is

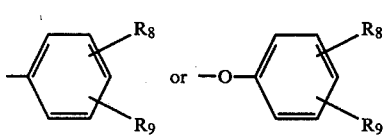

where $R_8$ and $R_9$ are each hydrogen, alkyl of 1 to 3 carbon atoms or alkoxy of 1 to 3 carbon atoms;

and non-toxic, pharmacologically acceptable acid addition salts thereof formed with inorganic or organic acids.

Specific examples of A, B, D, $R_3$, $R_4$, $R_5$ and $R_6$ are the following:

A and B together with each other and the respective carbon atoms to which they are attached and substituents $R_1$ and $R_2$:

Pyridine, phenyl, chlorophenyl, bromophenyl, fluorophenyl, aminophenyl, nitrophenyl, methoxyphenyl, ethoxyphenyl, propoxyphenyl, isopropoxyphenyl, dimethoxyphenyl, diethoxyphenyl, methoxy-ethoxyphenyl, methoxy-propoxyphenyl, ethoxy-isopropoxyphenyl, methoxy-chlorophenyl, ethoxybromophenyl and isopropoxy-fluorophenyl.

D: n-Propylene, n-butylene, 2-hydroxy-n-propylene, 2-hydroxy-n-butylene and 3-hydroxy-n-butylene group, $R_3$ and $R_5$: hydrogen, methyl, ethyl, propyl and isopropyl, $R_4$: hydrogen, methoxy, ethoxy, propoxy and isopropoxy.

$R_6$: methyl, ethyl, propyl, isopropyl, butyl, isobutyl, tert. butyl, pentyl, neopentyl, tert. pentyl, hexyl, 2-phenylethyl, 3-phenylpropyl, 4-phenylbutyl, 2-hydroxy-3-phenylpropyl, 2-hydroxy-4-phenylbutyl, 3-hydroxy-4-phenyl-butyl, 2-(methoxyphenyl)-ethyl, 3-(methoxyphenyl)-propyl, 4-(methoxyphenyl)-butyl, 2-hydroxy-3-(methoxyphenyl)-propyl, 2-(ethoxyphenyl)-ethyl, 3-(isopropoxyphenyl)-propyl, 2-(dimethoxyphenyl)-ethyl, 3-(dimethoxyphenyl)-propyl, 2-hydroxy-3-(dimethoxyphenyl)-propyl, 2-(methylphenyl)-ethyl, 2-(isopropylphenyl)-ethyl, 3-methylphenyl)-propyl, 2-hydroxy-3-(methylphenyl)-propyl, 4-(methylphenyl)-butyl, 2-(dimethylphenyl)-ethyl, 3-(dimethylphenyl)-propyl, 2-hydroxy-3-(dimethylphenyl)-propyl, 2-phenoxyethyl, 3-phenoxypropyl, 4-phenoxybutyl, 2-hydroxy-3-phenoxypropyl, 2-hydroxy-4-phenoxybutyl, 3-hydroxy-4-phenoxybutyl, 2-(methoxyphenoxy)-ethyl, 3-(methoxyphenoxy)-propyl, 4-(methoxyphenoxy)-butyl, 2-(ethoxyphenoxy)-ethyl; 3-(isopropoxyphenoxy)-propyl, 2-(dimethoxyphenoxy)-ethyl, 3-(dimethoxyphenoxy)-propyl, 2-hydroxy-3-(dimethoxyphenoxy)-propyl, 2-hydroxy-4-(dimethoxyphenoxy)-butyl, 2-(methylphenoxy)-ethyl, 2-(isopropylphenoxy)-ethyl, 3-(methylphenoxy)-propyl, 2-hydroxy-3-(methylphenoxy)-propyl, 4-(methylphenoxy)-butyl, 2-(dimethylphenoxy)-ethyl, 3-(dimethylphenoxy)-propyl, 2-hydroxy-3-(dimethylphenoxy)-propyl, 2-(methyl-methoxyphenyl)-ethyl, 3-(methylmethoxyphenyl)-propyl, 2-hydroxy-3-(methyl-methoxyphenyl)-propyl, 4-(methylmethoxyphenyl)-butyl, 2-(methyl-ethoxyphenyl)-ethyl, 3-(ethyl-ethoxyphenyl)-propyl, 2-hydroxy-3-(methyl-propoxyphenyl)-propyl, 2-(methyl-methoxyphenoxy)-ethyl, 3-(methyl-methoxyphenoxy)-propyl, 2-hydroxy-3-(methyl-methoxyphenoxy)-propyl, 4-(methyl-methoxyphenoxy)-butyl, 2-(isopropyl-methoxyphenoxy)-ethyl, 2-hydroxy-3-(methyl-isopropoxy-phenoxy)-propyl, and 2-hydroxy-3-(isopropyl-isopropoxy-phenoxy)-propyl.

A preferred subgenus under the genus defined by formula I is constituted by those compounds where A and B, together with each other and the respective carbon atoms to which they are attached, form a phenyl or pyridine ring;

$R_1$ is chlorine, methyl, methoxy or nitro;

$R_2$ is methoxy;

D is n-propylene, n-butylene, 2-hydroxy-n-propylene, 2-hydroxy-n-butylene or 3-hydroxy-n-butylene;

$R_3$ and $R_5$ are each alkyl of 1 to 3 carbon atoms or hydrogen;

$R_4$ is hydrogen or methoxy; and $R_6$ is alkyl of 4 carbon atoms, 2-(methoxy-phenyl)-ethyl, 2-(dimethoxy-phenyl)-ethyl, 2-(methyl-phenoxy)-ethyl, 2-(methoxy-phenoxy)-ethyl, 2-hydroxy-3-(methoxy-phenoxy)-propyl or 2-hydroxy-3-(methyl-phenoxy)-propyl;

and non-toxic, pharmacologically acceptable acid addition salts thereof.

An especially preferred subgenus is constituted by compounds of the formula I where A and B, together with each other and the respective carbon atoms to which they are attached and substituents $R_1$ and $R_2$ are phenyl, methoxyphenyl, dimethoxyphenyl or pyridine;

D is n-propylene or 2-hydroxy-n-propylene;

$R_3$ is hydrogen or methyl;

$R_4$ is hydrogen or methoxy;
$R_5$ is hydrogen or alkyl of 1 to 3 carbon atoms; and
$R_6$ is alkyl of 1 to 4 carbon atoms, 2-(methoxy-phenyl)-ethyl, 2-(dimethoxy-phenyl)-ethyl, 2-(methyl-phenoxy)-ethyl, 2-(methoxy-phenoxy)-ethyl, 2-hydroxy-3-(methoxy-phenoxy)-propyl or 2-hydroxy-3-(methyl-phenoxy)-ethyl;
and non-toxic, pharmacologically acceptable acid addition salts thereof.

A further particularly preferred subgenus is constituted by the compounds of the formula

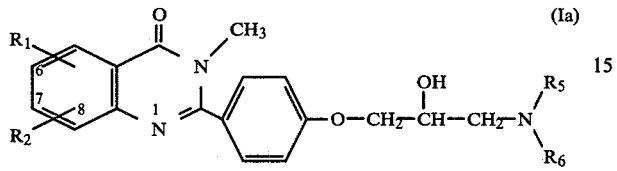

wherein
$R_1$ is 6- or 8-methoxy;
$R_2$ is hydrogen or 7-methoxy; and
$R_5$ and $R_6$, together with the nitrogen atom to which they are attached, are isopropylamino, tert. butylamino, N-methyl-N-[2-(3,4-dimethoxy-phenyl)-ethyl]-amino, 2-(2-methoxy-phenyl)-ethylamino, 2-(2-methyl-phenoxy)-ethylamino or 2-(2-methoxy-phenoxy)-ethylamino;
and non-toxic, pharmacologically acceptable acid addition salts thereof.

The compounds embraced by formula I may be prepared by the following methods:

METHOD A

By reacting a compound of the formula

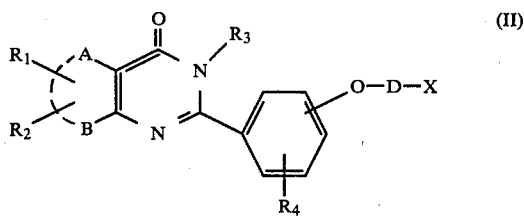

wherein
A, B, D, $R_1$, $R_2$, $R_3$ and $R_4$ have the same meanings as in formula I, and
X is a nucleophilic exchangeable substituent, such as halogen, or, together with the terminal and β-carbon atom of D, forms an epoxy group;
with an amine of the formula

wherein $R_5$ and $R_6$ have the same meanings as in formula I.

The reaction is advantageously carried out in a solvent such as ethanol, isopropanol, tetrahydrofuran, toluene, dimethylformamide or dimethylsulfoxide, optionally in the presence of an acid-binding agent, for instance on alcoholate or alkali metal carbonate such as potassium tert. butylate or potassium carbonate, and optionally in a closed vessel at temperatures between 50° and 200° C., but preferably at temperatures between 70° and 150° C. It is of particular advantage to carry out the reaction by using as the solvent an excess of the amine of the formula III.

METHOD B

By alkylating a compound of the formula

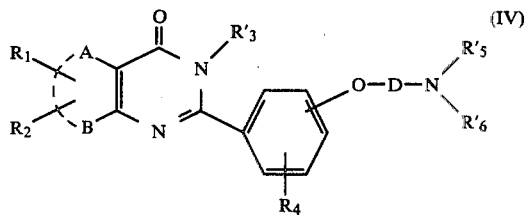

wherein
A, B, D, $R_1$, $R_2$ and $R_4$ have the same meanings as in formula I, and
at least one of the substituents $R_3'$, $R_5'$ and $R_6'$ is hydrogen and the others have the meanings defined for $R_3$, $R_5$ and $R_6$, respectively, in formula I,
with a compound of the formula

$$Z-Y \qquad (V)$$

wherein
Y has the meanings previously defined for $R_3$, $R_5$ and $R_6$ except hydrogen; and
Z is a nucleophilic exchangeable group, for instance halogen, such as chlorine, bromine or iodine, methylsulfonyloxy, p-toluenesulfonyloxy or methoxysulfonyloxy, or together with the terminal and β-carbon-atom of $R_6$ forms an epoxy group;
or with formaldehyde/formic acid.

The alkylation is preferably carried out in a solvent, such as acetone, tetrahydrofuran, dioxane, dimethylformamide or dimethylsulfoxide, with a corresponding alkyl halide, for instance with methyl iodide, ethyl bromide, tert. butyl chloride, 2-(2-methoxyphenyl)-ethyl bromide, 2-(2-methylphenoxy)-ethyl bromide or 1-chloro-2-hydroxy-3-(4-metyoxyphenoxy)-propane, with a corresponding sulfonyloxy compound, for example with dimethylsulfate, diethylsulfate or tert. butyl-p-toluene sulfonate, or with a corresponding epoxide such as 3-(4-methoxyphenoxy)-propyleneoxide, optionally in the presence of an inorganic or tertiary organic base, for instance in the presence of potassium carbonate, potassium tert. butylate, triethylamine or pyridine, where the latter may also serve as a solvent, at temperatures between 0° and 180° C., preferably, however, at the boiling point of the reaction mixture.

A methylation can also be carried out with formaldehyde-formic acid at elevated temperatures, preferably, however, at the boiling point of the reaction mixture.

The compounds of the formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, oxalic acid, maleic acid or the like.

The starting compounds of the formula II and III are either described in the literature or may be prepared be methods described in the literature.

Thus, for example a compound of the formula II can be obtained by reacting an oxazine [see J. Chem. Soc. 1972, 709; German Offenlegungsschrift 2,114,884; and Syn. Comm. 10, 241-243 (1980)] of the formula

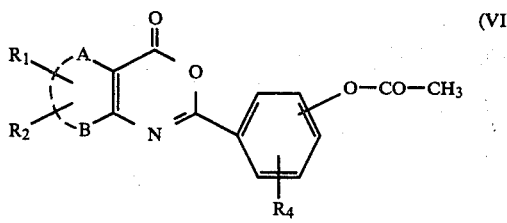

wherein A, B, R$_1$, R$_2$, and R$_4$ have the meanings previously defined, with an amine of the formula

wherein R$_3$ has the meanings previously defined, removing the acetyl radical, and alkylating the resulting intermediate with a halide of the formula

wherein D and X have the meanings previously defined.

A starting compound of the formula IV can be obtained, for example, by reacting a corresponding pyrimidine-4-one with a corresponding amine.

The following examples illustrate the present invention and will enable others skilled in the art to understand it more completely. It should be understood, however, that the invention is not limited solely to the particular examples given below.

The chemical structure of the novel compounds was confirmed by IR-, UV- and NMR-spectra and by elemental analysis.

Preparation of starting compounds

Example A 2-(4-Hydroxy-phenyl)-3-methyl-6-methoxy-3,4-dihydro-quinazolin-4-one (a) 2-(4-Acetoxy-phenyl)-6-methoxy-3,1-benzoxazin-4-one 16.7 gm (0.1 mol) of 3-methoxy-anthranilic acid were dissolved in 100 ml of pyridine, and the solution was mixed, while cooling and stirring, with 23.8 gm (0.1 mol+20%) of 4-acetoxy-benzoyl chloride. After 2 hours the reaction was finished, and the reaction mixture was poured into ice water. The crystalline precipitate thus formed was suction filtered off, dried and recrystallized from methanol.

M.p.: 164°-166° C.

Yield: 20.2 gm (65% of theory).

C$_{17}$H$_{13}$NO$_5$ (311.28): Calc.: C-65.59%; H-4.21%; N-4.50%. Found: C-65.51%; H-4.27%; N-4.58%.

(b) 2-(4-Hydroxy-phenyl)-3-methyl-6-methoxy-3,4-dihydro-quinazolin-4-one 6.2 gm (0.02 mol) of the product obtained in (a) were heated with 60 ml of a 40% methylamine solution in water in a steel cylinder at 120° C. After 3 hours the reaction was finished, the reaction solution was evaporated in vacuo and the obtained crude product was recrystallized from methanol.

M.p.: 146°-147° C.

Yield: 4.8 gm (85% of theory).

C$_{16}$H$_{14}$N$_2$O$_3$ (282.30): Calc.: C-68.08%; H-5.00%; N-9.92%. Found: C-67.95%; H-5.05%; N-9.86%.

Example B 2-(4-Hydroxy-phenyl)-3,6-dimethyl-3,4-dihydro-quinazolin-4-one (a) 2-(4-Acetoxy-phenyl)-6-methyl-3,1-benzoxazin-4-one 10 gm (0.066 mol) of 5-methyl-anthranilic acid were dissolved in 65 ml of pyridine, and the solution was mixed, while cooling and stirring, with 15.7 gm (0.066 mol+20%) of 4-acetoxy-benzoyl chloride. After 2 hours the reaction was finished, and the reaction mixture was poured into ice water. The crystalline precipitate thus formed was suction-filtered off, washed well with water and dried.

M.p.: 182°-184° C.

Yield: 17.2 gm (88% of theory).

C$_{17}$H$_{13}$NO$_4$ (295.29): Calc.: C-69.15%; H-4.44%; N-4.72%. Found: C-69.15%; H-4.61%; N-4.72%.

(b) 2-(4-Hydroxybenzoyl-amino)-5-methyl-benzoic acid monomethylamide 10 gm (0.034 mol) of the product obtained in (a) were heated in 100 ml of 30% methylamine solution in water on a steam bath. After 30 minutes the solution was evaporated in vacuo, and the white residue was dried.

M.p.: 250°-252° C.

Yield: 9.3 gm (97% of theory).

C$_{16}$H$_{16}$N$_2$O$_3$ (284.32): Calc.: C-67.59%; H-5.67%; N-9.85% Found: C-67.39%; H-5.88%; N-9.81%.

(c) 2-(4-Hydroxy-phenyl)-3,6-dimethyl-3,4-dihydro-quinazolin-4-one 5 gm (0.018 mol) of the product obtained in (b) were heated at 180° C. in 40 ml of ethylene glycol and 0.5 ml of N,N-dimethylamino-ethanol. After one hour the reaction was finished, the reaction solution was cooled and mixed with ice water, thereby the end product was obtained as crystals.

M.p.: 228°-230° C.

Yield: 4.2 gm (89% of theory).

C$_{16}$H$_{14}$N$_2$O$_2$ (266.30): Calc.: C-72.17%; H-5.30%; N-10.50% Found: C-72.13%; H-5.27%; N-10.52%.

Example C 2-(4-Hydroxy-phenyl)-3-methyl-6-methoxy-3,4-dihydro-quinazolin-4-one (a) 2-(4-Acetoxy-phenyl)-3-methyl-6-methoxy-3,4-dihydro-quinazolin-4-one A solution of 55.5 gm (0.332 mol) of 3-methoxy-anthranilic acid in 500 ml of pyridine, cooled to −30° C., was added at −30° C. to 91 gm (0.425 mol) of 4-acetoxy-phenylmethylimide chloride while stirring. The reaction mixture was stirred for one hour at 0° C. and for another hour at room temperature. Subsequently, the dark violet reaction mixture was poured into about 2.8 liters of ice water, whereby the desired product precipitated as violet crystals. The precipitate was suction-filtered off, washed with water and dried at 80° C. in a vacuum shelf-drier.

M.p.: 164°-170° C.

Yield: 80.4 gm (75.6% of theory).

C$_{18}$H$_{16}$N$_2$O$_4$ (324.33): Calc.: C-66.65%; H-4.97%; N-8.64% Found: C-66.29%; H:4.76%; N-8.53%.

(b) 2-(4-Hydroxy-phenyl)-3-methyl-6-methoxy-3,4-dihydro-quinazolin-4-one 80.3 gm (0.247 mol) of 2-(4-acetoxy-phenyl)-3-methyl-6-methoxy-3,4-dihydro-quinazolin-4-one were suspended in 800 ml of concentrated aqueous ammonia, and the suspension was heated for 1.5 hours on a steam bath, whereby at first a clear solution was obtained, and after about 60 minutes the formation of a white precipitate began. After cooling to 0° C., the product was suction-filtered off, washed with water and dried at 80° C. in a circulating air drier.

M.p.: 263°–268° C.

Yield: 65.7 gm (94% of theory).

$C_{16}H_{14}N_2O_3$ (282.29): Calc.: C-68.07%; H-5.00%; N-9.92%. Found: C-68.25%; H-5.16%; N-9.69%.

Example D 2-(4-Hydroxy-phenyl)-3methyl-3,4-dihydro-pyrido[2,3-e]-pyrimidin-4-one (a) 2-(4-Acetoxy-phenyl)-pyrido[5,6-b]-3,1-oxazin-4-one 27.6 gm (0.2 mol) of 2-amino-nicotinic acid were suspended in 250 ml of pyridine, and the suspension was mixed, while cooling and stirring, with 50.0 gm (0.25 mol) of 4-acetoxy-benzoyl chloride. After 2 hours the reaction was finished, and the mixture was poured into about 1.5 liters of ice water, whereby the desired product precipitated. The precipitate was suction-filtered off, washed well with water, and dried at 60° C. in a vacuum shelf-drier.

M.p.: 193°–196° C.

Yield: 43.5 gm (77% of theory).

$C_{15}H_{10}N_2O_4$ (282.25): Calc.: C-63.82%; H-3.57%; N-9.92%. Found: C-63.71%; H-3.51%; N-9.87%.

(b) 2-(4-Hydroxy-benzamido)-nicotinic acid methylamide 30 gm (0.106 mol) of the product obtained in (a) were heated on a steam bath in 300 ml of a 30% methylamine solution in water. After 10 minutes the solution was evaporated in vacuo, and the crystalline residue was boiled with about 300 ml of ethanol and then suction-filtered off. The obtained product was dried at 60° C. in a vacuum shelf-drier.

M.p.: 218°–220° C.

Yield: 19.8 gm (73% of theory).

$C_{14}H_{13}N_3O_3$ (271.26): Calc.: C-61.98%; H-4.83%; N-15.49%. Found: C-61.87%; H-4.69%; N-15.52%.

(c) 2-(4-Hydroxy-phenyl)-3-methyl-3,4-dihydro-pyrido[2,3-e]-pyrimidin-4-one 18.5 gm (0.068 mol) of the product obtained in (b) were heated for one hour in 200 ml of ethylene glycol and 4 ml of N,N-dimethylamino-ethanol at 180° C. After cooling, the reaction solution was poured into 1.5 liter of ice water. The end product which crystallized out was suction-filtered off, washed with a lot of water and dried at 60° C. in a vacuum shelf-drier.

M.p.: 256°–258° C.

Yield: 9.4 gm (54.6% of theory).

$C_{14}H_{11}N_3O_2$ (253.25): Calc.: C-66.39%; H-4.38%; N-16.59%. Found: C-66.43%; H:4.46%; N-16.62%.

Example E

2-[4-(4-Amino-butoxy)-phenyl]-3-methyl-6-methoxy-3,4-dihydro-quinazolin-4-one (a) 2-(4-Acetoxy-phenyl)-6-methoxy-3,1-benzoxazin-4-one 16.7 gm (0.1 mol) of 3-methoxy-anthranilic acid were dissolved in 100 ml of pyridine, and the solution was mixed, while cooling and stirring, with 23.8 gm (0.1 mol+20%) of 4-acetoxy-benzoyl chloride. After 2 hours the reaction was finished, and the reaction mixture was poured into ice water. The precipitate thus obtained was suction-filtered off, dried and recrystallized from methanol.

M.p.: 164°–166° C.

Yield: 20.2 gm (65% of theory).

$C_{17}H_{13}NO_5$ (311.28): Calc.: C-65.59%; H-4.21%; N-4.50%. Found: C-65.51%; H-4.27%; N-4.58%.

(b) 2-(4-Hydroxy-phenyl)-3-methyl-6-methoxy-3,4-dihydro-quinazolin-4one 6.2 gm (0.02 mol) of the product obtained in (a) were heated in a steel cylinder with 60 ml of a 40% methylamine solution in water at 120° C. After 3 hours the reaction was finished, the reaction solution was evaporated in vacuo, and the obtained crude product was recrystallized from methanol.

M.p.: 146°–147° C.

Yield: 4.8 gm (85% of theory).

$C_{16}H_{14}N_2O_3$ (282.30): Calc.: C-68.08%; H-5.00%; N-9.92%. Found: C-67.95%; H-5.05%; N-9.86%.

(c) 2-[4-(4-Chloro-butoxy)-phenyl]-3-methyl-6-methoxy-3,4-dihydro-quinazolin-4-one 4 gm (0.014 mol) of the product in (b) were dissolved in 30 ml of dimethylsulfoxide, and the solution was mixed, while stirring, with 1.75 gm (0.014 mol+10%) of potassium tert. butylate. Subsequently, 4 ml of 1-bromo-4-chlorobutane were added, and the reaction mixture was stirred at room temperature until the reaction was complete. The reaction mixture was poured into ice water, and the crystalline precipitate thus formed was suction-filtered off, washed well with water and dried.

M.p.: 127°–130° C.

Yield: 4.9 gm (94% of theory).

$C_{20}H_{21}ClN_2O_3$ (372.85): Calc.: C-64.43%; H-5.68%; N-7.15%; Cl-9.51%. Found: C-64.28%; H-5.61%; N-7.53%; Cl-9.59%.

(d) 2-[4-(4-Amino-butoxy)-phenyl]-3-methyl-6-methoxy-3,4-dihydro-quinazolin-4-one 4.5 gm (0.012 mol) of the product obtained in (c) were mixed with 2.2 gm (0.012 mol+10%) of 2,4-dimethoxybenzylamine, and the mixture was heated to 120° C. After 2 hours the reaction was complete, the obtained product was stirred at room temperature with 2 N hydrochloric acid, subsequently made alkaline with 2 N sodium hydroxide and extracted with methylene chloride. The combined organic extracts were dried over sodium sulfate and evaporated. The obtained crude product was purified on a silicagel column (particle size: 0.2–0.5 mm; eluant: methylene chloride:methanol=19:1). After evaporation, a colorless oil was obtained.

Yield: 2.6 gm (61% of theory).

$C_{20}H_{23}N_3O$ (353.42): Calc.: C-67.97%; H-6.56%; N-11.89%. Found: C-67.49%; H-6.49%; N-11.73%.

Preparation of the end product of formula I

EXAMPLE 1

2-[4-(2-Hydroxy-3-tert.butylamino-propoxy)-phenyl]-3-methyl-6-methoxy-3,4-dihydro-quinazolin-4-one (a) 2-[4-(1,2-Epoxy-propoxy)-phenyl]-3-methyl-6-methoxy-3,4-dihydro-quinazolin-4-one 2.8 gm (10 mmols) of 2-(4-hydroxyphenyl)-3-methyl-6-methoxy-3,4-dihydro-quinazolin-4-one were dissolved in 20 ml of dimethylsulfoxide, and the solution was mixed, while stirring, with 1.35 gm (10 mmols+20%) of potassium tert. butylate. Subsequently, 2.8 ml of epibromohydrin were added, and the reaction mixture was stirred at room temperature until the reaction had gone to completion. After pouring the reaction mixture into ice water, the crystalline precipitate formed thereby was suction-filtered off, washed well with water and dried.

M.p.: 194°–196° C.

Yield: 3.0 gm (89% of theory).

$C_{19}H_{18}N_2O_4$ (338.37): Calc.: C-67.44%; H-5.36%; N-8.28%. Found: C-67.41%; H-5.32%; N-8.27%.

(b) 2-[4-(2-Hydroxy-3-tert. butylamino-propoxy)-phenyl]-3-methyl-6-methoxy-3,4-dihydro-quinazolin-4-one 1.7 gm (5 mmols) of the epoxide obtained in (a) were heated in a steel cylinder with 17 ml of tert. butylamine at 120° C. for 3 hours. Thereafter, the excess amine was distilled off in vacuo, and the oily residue was recrystallized from acetone/ether.

M.p.: 154°–156° C.

Yield: 1.75 gm (83% of theory).

$C_{23}H_{29}N_3O_4$ (411.51): Calc.: C-67.13%; H-7.10%; N-10.21%. Found: C-67.10%; H-7.05%; N-10.19%.

EXAMPLE 2

2-{4-[2-Hydroxy-3-(2-(3,4-dimethoxyphenyl)-N-methyl-ethylamino)-propoxy]-phenyl}-3-methyl-6-methoxy-3,4-dihydro-quinazolin-4-one and its dihydrochloride 1.7 gm (5 mmols) of the 2-[4-(1,2-epoxy-propoxy)-phenyl]-3-methyl-6-methoxy-3,4-dihydro-quinazolin-4-one obtained in Example 1(a) were reacted at 120° C. with 1.7 gm of N-methyl-2-(3,4-dimethoxy-phenyl)-ethylamine. After the reaction had gone to completion the crude product thus obtained was purified on a silicagel column (particle size: 0.2–0.5 mm; eluant: methylene chloride/methanol=19:1). After evaporation of the eluate, the product thus obtained was dissolved in acetone, and the dihydrochloride was precipitated with ethereal hydrochloric acid.

M.p. of the dihydrochloride: 152°–155° C.

Yield: 1.7 gm (55% of theory).

$C_{30}H_{37}Cl_2N_3O_6$ (606.56): Calc.: C-59.40%; H-6.15%; N-6.93%; Cl-11.69%. Found: C-59.40%; H-6.17%; N-6.93%; Cl-11.39%.

EXAMPLE 3

2-{4-[3-(2-Hydroxy-3-(4-methoxyphenoxy)-propylamino)propoxy]-phenyl}-3-methyl-6-methoxy-3,4-dihydro-quinazolin-4-one (a) 2-[4-(3-Chloro-propoxy)-phenyl]-3-methyl-6-methoxy-3,4-dihydro-quinazolin-4-one 2.8 gm (10 mmols) of 2-(4-hydroxy-phenyl)-3-methyl-6-methoxy-3,4-dihydro-quinazolin-4-one were dissolved in 20 ml of dimethylsulfoxide, and the solution was mixed, while stirring, with 1.35 gm (10 mmols+20%) of potassium tert. butylate. Subsequently, 2.8 ml of 1-bromo-3-chloropropane were added, and the mixture was stirred at room temperature until the reaction was complete. The reaction mixture was then poured into ice water, the aqueous mixture was extracted with ethyl acetate, and the combined organic extracts were evaporated in vacuo after drying over sodium sulfate. The resulting oil, which solidified into crystals, was recrystallized from acetone/ether.

M.p.: 114°–116° C.

Yield: 3.1 gm (86% of theory).

$C_{19}H_{19}ClN_2O_3$ (358.82): Calc.: C-63.60%; H-5.34%; N-7.81%; Cl-9.88%. Found: C-63.47%; H-5.28%; N-7.88%; Cl-9.74%.

(b) 2-{4-[3-(2-Hydroxy-3-(4-methoxy-phenoxy)-propylamino)propoxy]-phenyl}-3-methyl-6-methoxy-3,4-dihydro-quinazolin-4-one 1.8 gm (5 mmols) of the propyl chloride obtained in 3(a) were mixed with 1.8 gm of 2-hydroxy-3-(4-methoxyphenoxy)-propylamine, and the mixture was allowed to react at 140° C. After the reaction was complete, the crude product thus obtained was purified on a silicagel column (particle size: 0.2–0.5 mm; eluant: methylene chloride/methanol=19:1). After evaporation of the eluate, the resulting colorless oil was recrystallized from acetone/ether.

M.p.: 134°–136° C.

Yield: 1.9 gm (73% of theory).

$C_{29}H_{33}N_3O_6$ (519.60): Calc.: C-67.04%; H-6.40%; N-8.09%. Found: C-66.96%; H-6.41%; N-8.10%.

Similar yields were obtained when the reaction was carried out at 80° C. in ethanol or at 110° C. in toluene.

EXAMPLE 4

2-[4-(2-Hydroxy-3-tert.butylamino-propoxy)-phenyl]-6-methoxy-3,4-dihydro-quinazolin-4-one (a) 2-[4-(1,2-Epoxy-propoxy)-phenyl]-6-methoxy-3,4-dihydro-quinazolin-4-one 4.5 gm (16.7 mmols) of 2-(4-hydroxy-phenyl)-6-methoxy-3,4-dihydro-quinazolin-4-one were dissolved in 50 ml of sulfolane, and the solution was mixed, while stirring, with 2.55 gm (16.7 mmols+10%) of potassium carbonate. After a clear solution was formed, 4.5 ml of epibromohydrin were added, and the mixture was stirred at room temperature until the reaction was complete. The reaction mixture was poured into ice water, and the resulting crystalline precipitate was suction-filtered off, washed well with water and dried.

M.p.: 102°–105° C.

Yield: 4.8 gm (89% of theory).

$C_{18}H_{16}N_2O_4$ (324.34): Calc.: C-66.66%; H-4.97%; N-8.64%. Found: C-66.38%; H-4.92%; N-8.57%.

(b) 2-[4-(2-Hydroxy-3-tert. butylamino-propoxy)-phenyl]-6-methoxy-3,4-dihydro-quinazolin-4-one 2.3 gm (8.5 mmols) of the epoxide obtained in Example 4(a) were heated in a steel cylinder with 23 ml of tert.butylamine at 120° C. After 3 hours the reaction was complete. The excess amine was distilled off, and the resulting crude crystalline product was recrystallized from acetone/ether.

M.p.: 189°–191° C.

Yield: 2.2 gm (64.7% of theory).

$C_{22}H_{27}N_3O_4$ (397.46): Calc.: C-66.48%; H-6.85%; N-10.57%. Found: C-66.16%; H-6.88%; N-10.38%.

EXAMPLE 5

2-[4-(3-tert.Butylamino-propoxy)-phenyl]-8-methoxy-3,4-dihydro-quinazolin-4-one and its dihydrochloride (a) 2-[4-(3-Chloro-propoxy)-phenyl]-8-methoxy-3,4-dihydro-quinazolin-4-one 2.7 gm (10 mmols) of 2-(4-hydroxy-phenyl)-6-methoxy-3,4-dihydro-quinazolin-4-one were dissolved in 30 ml of sulfolane, and the solution was mixed with 1.5 gm (10 mmols+10%) of potassium carbonate. The resulting clear solution was admixed with 2.7 ml of 1-bromo-3-chloropropane, and the reaction mixture was stirred until the reaction was complete. After pouring it into ice water, the aqueous mixture was extracted with ethyl acetate, and the combined organic extracts were dried over sodium sulfate and evaporated. A colorless oil was obtained, which crystallized upon cooling.

M.p.: 50°–55° C.

Yield: 3.0 gm (88% of theory).

$C_{18}H_{17}ClN_2O_3$ (344.80): Calc.: C-62.70%; H-4.97%; N-8.12%; Cl-10.28%. Found: C-62.45%; H-4.84%; N-8.07%; Cl-10.09%.

(b) 2-[4-(3-tert.Butylamino-propoxy)-phenyl]-8-methoxy-3,4-dihydro-quinazolin-4-one 1.5 gm (4.4 mmols) of the product obtained in (a) were reacted in a steel cylinder with 15 ml of tert. butylamine at 120° C. After the reaction was complete, the excess amine was distilled off in vacuo, and the residue was purified on a silicagel column (particle size: 0.2–0.5 mm; eluant: methylene chloride/methanol = 19:1). After evaporation of the eluate, the resulting colorless oil was dissolved in acetone and the dihydrochloride was precipitated with ethereal hydrochloric acid.

M.p. of the dihydrochloride: 133°–135° C.

Yield: 1.7 gm (85% of theory).

$C_{22}H_{29}Cl_2N_3O_3$ (454.60): Calc.: C-58.15%; H-6.43%; N-9.25%; Cl-15.61%. Found: C-58.03%; H-6.40%; N-9.16%; Cl-15.34%.

EXAMPLE 6

2-{4-[2-Hydroxy-3-(2-(2-methoxy-phenyl)-ethylamino)-propoxy]-phenyl}-3-methyl-6-methoxy-3,4-dihydro-quinazolin-4-one This compound was prepared analogous to Example 2 from 2-[4-(1,2-epoxy-propoxy)-phenyl]-3-methyl-6-methoxy-3,4-dihydro-quinazolin-4-one and 2-(2-methoxyphenyl)-ethylamine.

M.p. of the dihydrochloride: 156°–158° C.

Yield: 41% of theory.

$C_{28}H_{33}Cl_2N_3O_5$ (562.50): Calc.: C-59.79%; H-5.91%; N-7.47%; Cl-12.61%. Found: C-59.80%; H-5.86%; N-7.45%; Cl-12.49%.

EXAMPLE 7

2-[4-(2-Hydroxy-3-diethylamino-propoxy)-phenyl]-3-methyl-6-methoxy-3,4-dihydro-quinazolin-4-one This compound was prepared analogous to Example 1 from 2-[4-(1,2-epoxy-propoxy)-phenyl]-3-methyl-6-methoxy-3,4-dihydro-quinazolin-4-one and diethylamine.

M.p.: 123°–125° C. (acetone/ether).

Yield: 52% of theory.

$C_{23}H_{29}N_3O_4$ (411.51): Calc.: C-67.14%; H-7.10%; N-10.21%; Found: C-67.09%; H-7.06%; N-10.18%.

EXAMPLE 8

2-[4-(2-Hydroxy-3-isopropylamino-propoxy)-phenyl]-3-methyl-6-methoxy-3,4-dihydro-quinazolin-4-one This compound was prepared analogous to Example 1 from 2-[4-(1,2-epoxy-propoxy)-phenyl]-3-methyl-6-methoxy-3,4-dihydro-quinazolin-4-one and isopropylamine.

M.p.: 130°–132° C.

Yield: 53% of theory.

$C_{22}H_{27}N_3O_4$ (397.48): Calc.: C-66.47%; H-6.84%; N-10.57%. Found: C-66.39%; H-6.86%; N-10.60%.

EXAMPLE 9

2-[4-(2-Hydroxy-3-isopropylamino-propoxy)-phenyl]-6-methoxy-3,4-dihydro-quinazolin-4-one This compound was prepared analogous to Example 4 from 2-[4-(1,2-epoxy-propoxy)-phenyl]-6-methoxy-3,4-dihydro-quinazolin-4-one and isopropylamine.

M.p.: 198°–201° C.

Yield: 42% of theory.

$C_{21}H_{25}N_3O_4$ (383.45): Calc.: C-65.78%; H-6.57%; N-10.96%. Found: C-65.59%; H-6.42%; N-10.73%.

EXAMPLE 10

2-{4-[2-Hydroxy-3-(2-(2-methoxy-phenyl)-ethylamino)-propoxy]-phenyl}-3-methyl-8-methoxy-3,4dihydro-quinazolin-4-one This compound was prepared analogous to Example 2 from 2-[4-(1,2-epoxy-propoxy)-phenyl]-3-methyl-8-methoxy-3,4-dihydro-quinazolin-4-one and 2-(2-methoxy-phenyl)-ethylamine.

M.p. of the dihydrochloride: 120°–125° C.

Yield: 62% of theory.

$C_{28}H_{33}Cl_2N_3O_5$ (562.50): Calc.: C-59.79%; H-5.91%; N:7.47%; Cl-12.61%. Found: C-59.52%; H-5.86%; N-7.41%; Cl-12.48%.

EXAMPLE 11

2-[4-(2-Hydroxy-3-diethylamino-propoxy)-phenyl]-3-methyl-8-methoxy-3,4-dihydro-quinazolin-4-one This compound was prepared analogous to Example 1 from 2-[4-(1,2-epoxy-propoxy)-phenyl]-3-methyl-8-methoxy-3,4-dihydro-quinazolin-4-one and diethylamine.

M.p. of the dihydrochloride: 127°–133° C.

Yield: 71% of theory.

$C_{23}H_{31}Cl_2N_3O_4$ (484.43): Calc.: C-57.03%; H-6.45%; N-8.67%; Cl-14.64%. Found: C-57.11%; H-6.41%; N-8.63%; Cl-14.28%.

EXAMPLE 12

2-{4-[2-Hydroxy-3-(2-(2-methyl-phenoxy)-ethylamino)-propoxy]-phenyl}-3-methyl-8-methoxy-3,4-dihydro-quinazolin-4-one This compound was prepared analogous to Example 2 from 2-[4-(1,2-epoxy-propoxy)-phenyl]-3-methyl-8-methoxy-3,4-dihydro-quinazolin-4-one and 2-(2-methyl-phenoxy)-ethylamine.

M.p. of the hydrochloride: 120°–125° C.

Yield: 45% of theory.

$C_{28}H_{32}ClN_3O_5$ (526.04): Calc.: C-63.93%; H-6.13%; N-7.99%; Cl-6.73%. Found: C-63.81%; H-6.04%; N-8.03%; Cl-6.84%.

EXAMPLE 13

2-{4-[3-(2-Hydroxy-3-(3-methyl-phenoxy)-propylamino)-propoxy]-phenyl}-3-methyl-8-methoxy-3,4-dihydro-quinazoline-4-one This compound was prepared analogous to Example 3 from 2-[4-(3-chloro-propoxy)-phenyl]-3-methyl-8-methoxy-3,4-dihydro-quinazolin-4-one and 2-hydroxy-3-(2-methyl-phenoxy)-propylamine.

M.p.: 138°–140° C.

Yield: 63% of theory.

$C_{29}H_{33}N_3O_5$ (503.60): Calc.: C-69.16%; H-6.60%; N-8.34%. Found: C-68.98%; H-6.64%; N-8.33%.

EXAMPLE 14

2-{4-[2-Hydroxy-3-(2-(2-methoxy-phenyl)-ethylamino)-propoxy]-phenyl}-3-methyl-6,7-dimethoxy-3,4-dihydro-quinazolin-4-one This compound was prepared analogous to Example 2 from 2-[4-(1,2-epoxy-propoxy)-phenyl]-3-methyl-6,7-dimethoxy-3,4-dihydro-quinazolin-4-one and 2-(2-methoxy-phenyl)-ethylamine.

M.p. of the trihydrochloride: 188°–192° C.
Yield: 29% of theory.
$C_{29}H_{36}Cl_3N_3O_6$ (628.96): Calc. C-55.37%; H-5.76%; N-6.68%; Cl-16.91%. Found: C-55.51%; H-5.75%; N-6.67%; Cl-16.20%.

EXAMPLE 15

2-{4-[2-Hydroxy-3-(2-(2-methyl-phenoxy)-ethylamino)-propoxy]-phenyl}-3-methyl-6,7-dimethoxy-3,4-dihydro-quinazolin-4-one This compound was prepared analogous to Example 2 from 2-[4-(1,2-epoxy-propoxy)-phenyl]-3-methyl-6,7-dimethoxy-3,4-dihydro-quinazolin-4-one and 2-(2-methyl-phenoxy)-ethylamine.

M.p.: 195°–198° C.
Yield: 13% of theory.
$C_{29}H_{33}N_3O_6$ (519.57): Calc.: C-67.03%; H-6.40%; N-8.09%. Found: C-67.23%; H-6.53%; N-8.13%.

EXAMPLE 16

2-[4-(3-tert.Butylamino-propoxy)-phenyl]-3-methyl-6,7-dimethoxy-3,4-dihydro-quinazolin-4-one This compound was prepared analogous to Example 3 from 2-[4-(3-chloro-propoxy)-phenyl]-3-methyl-6,7-dimethoxy-3,4-dihydro-quinazolin-4-one and tert. butylamine.

M.p. of the hydrochloride: 283°–286° C.
Yield: 78% of theory.
$C_{24}H_{32}ClN_3O_4$ (461.97): Calc.: C-62.39%; H-6.98%; N-9.10%; Cl-7.67%. Found: C-62.18%; H-6.92%; N-9.15%; Cl-7.80%.

EXAMPLE 17

2-{4-[3-(2-Hydroxy-3-(3-methyl-phenoxy)-propylamino)-propoxy]-phenyl}-3-methyl-6,7-dimethoxy-3,4-dihydro-quinazolin-4-one This compound was prepared analogous to Example 3 from 2-[4-(3-chloro-propoxy)-phenyl]-3-methyl-6,7-dimethoxy-3,4-dihydro-quinazolin-4-one and 2-hydroxy-3-(2-methyl-phenoxy)-propylamine.

M.p. of the hydrochloride: 222° C.
Yield: 22% of theory.
$C_{30}H_{36}ClN_3O_6$ (570.07): Calc.: C-63.20%; H-6.36%; N-7.37%; Cl-6.22%. Found: C-62.91%; H-6.51%; N-7.27%; Cl-6.50%.

EXAMPLE 18

2-[3-Methoxy-4-(2-hydroxy-3-tert.butylamino-propoxy)-phenyl]-3-methyl-6-methoxy-3,4-dihydro-quinazolin-4-one This compound was prepared analogous to Example 1 from 2-[3-methoxy-4-(1,2-epoxy-propoxy)-phenyl]-3-methyl-6-methoxy-3,4-dihydro-quinazolin-4-one and tert. butylamine.

M.p.: 100°–105° C. (acetone/ether).
Yield: 73% of theory.
$C_{24}H_{31}N_3O_5$ (441.53): Calc.: C-65.29%; H-7.08%; N-9.52%. Found: C-65.27%; H-7.12%; N-9.38%.

EXAMPLE 19

2-[4-(2-Hydroxy-3-tert.butylamino-propoxy)-phenyl]-3-methyl-6-nitro-3,4-dihydro-quinazolin-4-one This compound was prepared analogous to Example 1 from 2-[4-(1,2-epoxy-propoxy)-phenyl]-3-methyl-6-nitro-3,4-dihydro-quinazolin-4-one and tert.butylamine.

M.p.: 267°–270° C. (acetone/ether).
Yield: 31% of theory.
$C_{22}H_{26}N_4O_5$ (426.48): Calc.: C-61.96%; H-6.15%; N-13.14%. Found: C-61.83%; H-6.07%; N-12.97%.

EXAMPLE 20

2-[4-(2-Hydroxy-3-tert.butylamino-propoxy)-phenyl]-3,6-dimethyl-3,4-dihydro-quinazolin-4-one This compound was prepared analogous to Example 1 from 2-[4-(1,2-epoxy-propoxy)-phenyl]-3,6-dimethyl-3,4-dihydro-quinazolin-4-one and tert. butylamine.

M.p.: 146°–150° C. (acetone/ether).
Yield: 88% of theory.
$C_{23}H_{29}N_3O_5$ (395.51): Calc.: C-69.85%; H-7.39%; N-10.62%. Found: C-69.58%; H-7.29%; N-10.52%.

EXAMPLE 21

2-[4-(2-Hydroxy-3-isopropylamino-propoxy)-phenyl]-3,6-dimethyl-3,4-dihydro-quinazolin-4-one This compound was prepared analogous to Example 1 from 2-[4-(1,2-epoxy-propoxy)-phenyl]-3,6-dimethyl-3,4-dihydro-quinazolin-4-one and isopropylamine.

M.p.: 147°–153° C. (acetone/ether).
Yield: 87% of theory.
$C_{22}H_{27}N_3O_3$ (381.48): Calc.: C-69.27%; H-7.14%; N-11.02%. Found: C-69.21%; H-7.23%; N-11.07%.

EXAMPLE 22

2-[4-(2-Hydroxy-3-tert. butylamino-propoxy)-phenyl]-3-methyl-6-chloro-3,4-dihydro-quinazolin-4-one This compound was prepared analogous to Example 1 from 2-[4-(1,2-epoxy-propoxy)-phenyl]-3-methyl-6-chloro-3,4-dihydro-quinazolin-4-one and tert. butylamine.

M.p.: 166°–168° C. (acetone/ether).
Yield: 80% of theory.
$C_{22}H_{26}ClN_3O_3$ (415.92): Calc.: C-63.53%; H-6.30%; N-10.10%; Cl-8.52%. Found: C-64.18%; H-5.79%; N-10.67%; Cl-8.40%.

EXAMPLE 23

2-[4-(3-Diethylamino-propoxy)-phenyl]-3-methyl-3,4-dihydro-quinazolin-4-one hydroiodide 0.9 gm (0.0025 mol) of 2-[4-(3-diethylamino-propoxy-phenyl]-3,4-dihydro-quinazolin-4-one were dissolved, while stirring, in 10 ml of dimethylsulfoxide at 60° C., the solution was cooled to room temperature, and 0.34 gm (0.003 mol) of potassium tert. butylate were added. After 15 minutes, 0.9 ml of methyl iodide were added dropwise thereto, stirring was continued for 2 hours at room temperature, and the reaction mixture was then poured into 100 ml of acetone. While stirring and adding of about 20 ml of ether, the desired product precipitated, and the white crystals were suction-filtered off, washed with ether and dried at 50° C. in a circulating air drier.

M.p.: 218°–222° C.
Yield: 0.8 gm (67% of theory).
$C_{22}H_{27}N_3O_2 \cdot xHI$ (493.38): Calc.: C-53.55%; H-5.71%; N-8.51%; H-25.72%. Found: C-53.58%; H-6.00%; N-8.21%; H-25.50%.

EXAMPLE 24

2-[4-(2-Hydroxy-3-isopropylamino-propoxy)-phenyl]-3-methyl-3,4-dihydro-pyrido[2,3-e]pyrimidin-4-one dihydrochloride (a) 2-[4-(1,2-Epoxy-propoxy)-phenyl]-3-methyl-3,4-dihydro-pyrido[2,3-e]pyrimidin-4-one 9.4 gm (0.037 mol) of 2-(4-hydroxy-phenyl)-3-methyl-3,4-dihydro-pyrido[2,3-e]-pyrimidin-4-one were dissolved in 100 ml of dimethylsulfoxide, and the solution was mixed, while stirring with 4.5 gm (0.04 mol) of potassium tert. butylate. After a clear solution was formed, 9.4 ml of epibromohydrin were added, and the reaction mixture was stirred for one hour at room temperature. Thereafter, it was poured into 600 ml of ice water, and the resulting crystalline product was suction-filtered off and dried at 40° C. in a vacuum shelf-drier.
M.p.: 92°–95° C.
Yield: 9.3 gm (81% of theory).
$C_{17}H_{15}N_3O_5$ (309.31): Calc.: C-66.00%; H-4.89%; N-13.58%. Found: C-66.13%; H-4.96%; N-13.42%.

(b) 2-[4-(2-Hydroxy-3-isopropylamino-propoxy)-phenyl]-3-methyl-3,4-dihydro-pyrido[2,3-e]-pyrimidin-4-one-dihydrochloride 2.9 gm (0.009 mol) of the product obtained in (a) were reacted with 30 ml of isopropylamine in a steel cylinder at 120° C. After the reaction was complete, the excess amine was distilled off in vacuo, and the residue was purified on a silicagel column (particle size: 0.2–0.5 mm; eluant: methylene chloride/methanol=19:1). After evaporation of the eluate, the residual colorless oil was dissolved in 50 ml of acetone, and the dihydrochloride was precipitated with ethereal hydrochloric acid.
M.p. of the dihydrochloride: 142°–145° C.
Yield: 2.0 gm (50% of theory).
$C_{20}H_{26}Cl_2N_4O_3$ (441.37): Calc.: C-54.42%; H-5.94%; N-12.69%; Cl-16.07%. Found: C-54.20%; H-6.11%; N-12.87%; Cl-16.00%.

EXAMPLE 25

2-[4-(2-Hydroxy-3-tert.butylamino-propoxy)-phenyl]-3-methyl-3,4-dihydro-pyrido[2,3-e]pyrimidin-4-one dihydrochloride This compound was prepared analogous to Example 24 from 2-[4-(1,2-epoxy-propoxy)-phenyl]-3-methyl-3,4-dihydro-pyrido[2,3-e]pyrimidin-4-one and tert.butylamine.
M.p. of the dihydrochloride: 168°–171° C.
Yield: 34% of theory.
$C_{21}H_{28}Cl_2N_4O_3$ (455.37): Calc.: C-55.38%; H-6.19%; N-12.30%; Cl-15.57%. Found: C-55.30%; H-6.25%; N-12.26%; Cl-15.52%.

EXAMPLE 26

2-{4-[2-Hydroxy-3-(2-(4-methoxy-phenoxy)-ethylamino)-propoxy]-phenyl}-3-methyl-3,4-dihydro-pyrido[2,3-e]-pyrimidin-4-one This compound was prepared analogous to Example 24 from 2-[4-(1,2-epoxy-propoxy)-phenyl]-3-methyl-3,4-dihydro-pyrido[2,3-e]pyrimidin-4-one and 2-(4-methoxy-phenoxy)ethylamine.
M.p.: 132°–135° C.
Yield: 17% of theory.
$C_{26}H_{28}N_4O_5$ (476.51): Calc.: C-65.53%; H-5.92%; N-11.75%. Found: C-65.42%; H-6.06%; N-11.87%.

EXAMPLE 27

2-[4-(2-Hydroxy-3-isopropylamino-propoxy)-phenyl]-3-methyl-3,4-dihydro-pyrido[3,4-e]pyrimidin-4-one dihydrochloride This compound was prepared analogous to Example 24 from 2-[4-(1,2-epoxy-propoxy)-phenyl]-3-methyl-3,4-dihydro-pyrido[3,4-e]pyrimidin-4-one and isopropylamine.
M.p. of the dihydrochloride: 122°–125° C.
Yield: 68% of theory.
$C_{20}H_{26}Cl_2N_4O_3$ (441.35): Calc.: C-54.42%; H-5.94%; N-12.69%; Cl-16.06%. Found: C-54.39%; H-5.88%; N-12.74%; Cl-16.02%.

EXAMPLE 28

2-[4-(2-Hydroxy-3-tert.butylamino-propoxy)-phenyl]-3-methyl-3,4-dihydro-pyrido[3,4-e]pyrimidin-4-one dihydrochloride This compound was prepared analogous to Example 24 from 2-[4-(1,2-epoxy-propoxy)-phenyl]-3-methyl-3,4-dihydro-pyrido[3,4-e]pyrimidin-4-one and tert. butylamine.
M.p. of the dihydrochloride: 171°–173° C.
Yield: 66.6% of theory.
$C_{21}H_{28}Cl_2N_4O_3$ (455.37): Calc.: C-55.38%; H-6.19%; H-12.30%; Cl-15.57%. Found: C-55.24%; H-6.24%; H-12.43%; Cl-15.70%.

EXAMPLE 29

2-{4-[4-(2-Hydroxy-3-(4-methoxy-phenoxy)-propylamino)butoxy]-phenyl}-3-methyl-6-methoxy-3,4-dihydro-quinazolin-4-one and its hydrochloride 2.5 gm (0.007 mol) of 2-[4-(4-amino-butoxy)-phenyl]-3-methyl-6-methoxy-3,4-dihydro-quinazolin-4-one were reacted at 120° C. with 1.5 gm (0.007 mol+20%) of 1,2-epoxy-3-(4-methoxy-phenoxy)-propane. After 3 hours the reaction was complete, and the thus obtained crude product was purified on a silicagel column (particle size: 0.2–0.5 mm; eluant: methylene chloride/methanol=49:1). After evaporation of the eluate, the residual yellowish oil was dissolved in acetone, and the hydrochloride was precipitated with ethereal hydrochloric acid.
M.p. of the hydrochloride: 105°–107° C.
Yield: 2.3 gm (57% of theory).
$C_{30}H_{36}ClN_3O_5$ (570.08): Calc.: C-63.20%; H-6.36%; N-7.37%; Cl-6.22%. Found: C-63.12%; H-6.18%; N-7.28%; Cl-6.14%.

EXAMPLE 30

2-{4-[3-(2-Hydroxy-3-(4-methoxy-phenoxy)-propylamino)propoxy]-phenyl}-8-methoxy-3,4-dihydro-quinazolin-4-one and its dihydrochloride (a) 2-[4-(3-Chloro-propoxy)-phenyl]-8-methoxy-3,4-dihydro-quinazolin-4-one 2.7 gm (10 mmols) of 2-(4-hydroxy-phenyl)-8-methoxy-3,4-dihydro-quinazolin-4-one were dissolved in 30 ml of sulfolane and reacted with 1.5 gm (10 mmols+10%) of potassium carbonate. The resulting clear solution was admixed with 2.7 ml of 1-bromo-3-chloro-propane, and the mixture was stirred at room temperature until the reaction was complete. The reaction mixture was then poured into ice water, the aqueous mixture was extracted with ethyl acetate, and the combined organic extracts were dried over sodium sulfate and evaporated. A colorless oil was obtained, which crystallized upon cooling.

M.p.: 50°-55° C.

Yield: 3.0 gm (88% of theory).

$C_{18}H_{17}ClN_2O_3$ (344.80): Calc.: C-62.70%; H-4.97%; N-8.12%; Cl-10.28%. Found: C-62.45%; H-4.84%; N-8.07%; Cl-10.09%.

(b) 2-{4-[3-(2-Hydroxy-3-(4-methoxy-phenoxy)-propylamino)propoxy]-phenyl}-8-methoxy-3,4-dihydro-quinazolin-4-one 1.5 gm (4.4 mmols) of the product obtained in (a) were reacted at 120° C. with 1.05 gm (4.4 mmols+10%) of 2-hydroxy-3-(4-methoxy-phenoxy)-propylamine. After the reaction was complete, the crude product thus obtained was purified on a silicagel column (particle size: 0.2-0.5 mm; eluant: methylene chloride/methanol=19:1). After evaporation of the eluate, the yellow oil which remained was dissolved in acetone, and the hydrochloride was precipitated with ethereal hydrochloric acid.

M.p. of the dihydrochloride: 190°-193° C.

Yield: 1.4 gm (56% of theory). $C_{28}H_{33}Cl_2N_3O_6$ (578.60): Calc.: C-58.12%; H-5.75%; N-7.26%; Cl-12.26%. Found: C-58.34%; H-5.71%; N-7.34%; Cl-11.98%.

EXAMPLE 31

2-[4-(2-Hydroxy-3-tert.butylamino-propoxy)-phenyl]-3-isopropyl-6-methoxy-3,4-dihydro-quinazolin-4-one This compound was prepared analogous to Example 1 from 2-[4-(1,2-epoxy-propoxy)-phenyl]-3-isopropyl-6-methoxy-3,4-dihydro-quinazolin-4-one and tert. butylamine.

M.p.: 145°-147° C.

Yield: 78% of theory.

$C_{25}H_{33}N_3O_4$ (439.56): Calc.: C-65.62%; H-7.41%; N-9.18%. Found: C-65.49%; H-7.88%; N-9.20%.

EXAMPLE 32

2-{4-[2-Hydroxy-3-(2-(3,4-dimethoxy-phenyl)-N-propylethylamino)-propoxy]-phenyl}-3-methyl-6-methoxy-3,4-dihydro-quinazolin-4-one This compound was prepared analogous to Example 2 from 2-[4-(1,2-epoxy-propoxy)-phenyl]-3-methyl-6-methoxy-3,4-dihydro-quinazolin-4-one and N-propyl-2-(3,4-dimethoxyphenyl)-ethylamine.

M.p.: 112°-117° C.

Yield: 40% of theory.

$C_{32}H_{41}Cl_2N_3O_6$ (634.61): Calc.: C-60.56%; H-6.51%; N-6.62%; Cl-11.17%. Found: C-59.89%; H-6.79%; N-6.70%; Cl-11.15%.

The compounds of the present invention, that is, those embraced by formula I and their non-toxic, pharmacologically acceptable acid addition salts, have useful pharmacodynamic properties. More particularly, they exhibit hypotensive, antiarrhythmic and $\beta$-receptor-blocking activities in warm-blooded animals such as dogs.

The above properties of the compounds of the instant invention were ascertained by the pharmacological tests described below, and the results of these tests for a few representative species of the genus are shown in the tables, where A = 2-[4-(2-Hydroxy-3-tert.butylamino-propoxy)-phenyl]-3-methyl-6-methoxy-3,4-dihydro-quinazolin-4-one, B = 2-{4-[2-Hydroxy-3-(2-(3,4-dimethoxy-phenyl)-N-methylethylamino)-propoxy]-phenyl}-3-methyl-6-methoxy-3,4-dihydro-quinazolin-4-one dihydrochloride, C = 2-{4-[2-Hydroxy-3-(2-(2-methoxy-phenyl)-ethylamino)-propoxy]-phenyl}-3-methyl-6-methoxy-3,4-dihydroquinazolin-4-one dihydrochloride, D = 2-[4-(2-Hydroxy-3-isopropylamino-propoxy)-phenyl]-3-methyl-6-methoxy-3,4-dihydro-quinazolin-4-one, E = 2-{4-[2-Hydroxy-3-(2-(2-methyl-phenoxy)-ethylamino)-propoxy]-phenyl}-3-methyl-6,7-dimethoxy-3,4-dihydroquinazolin-4-one, and F = 2-{4-[3-(2-Hydroxy-3-(3-methyl-phenoxy)-propylamino)-propoxy]-phenyl}-3-methyl-8-methoxy-3,4-dihydroquinazolin-4-one.

1. Effect on blood circulation

The blood circulation tests were carried out on dogs with a body weight of 18-29 kg under chloraloseurethane-nembutal anesthesia (54+270+10 mg/kg i.v.). After opening the thorax in the 4th left intercostal space the animals were ventilated with room air by means of a Harvard respirator.

The arterial blood pressure was measured in the arteria carotis by a Statham pressure transducer; the heart rate was measured electronically from the sequence of the R-peaks of the electrocardiogram. The maximum rate of pressure increase (dp/dr max) in the left ventricula was measured by means of a Konigsberg pressure received and a Grass differential amplifier.

All parameters were recorded by means of a direct-writer. For anticoagulation the animals were injected i.v. with a solution of 10 mg/kg of sodium polyethylenesulfonate in 20% polydiol. The test compounds were administered intravenously to groups of 3 to 4 dogs.

The following table shows the results:

| Compound | Dosage mg/kg i.v. | Effect on average arterial blood pressure mm Hg | Decrease in heart rate 1/min | Decrease in contractility dp/dt max | Duration |
|---|---|---|---|---|---|
| A | 0.5 | −20/−8 | −21 | −33 | >55 |
| B | 1.0 | −16/−24 | −28 | −17 | 45 |
| C | 1.0 | +1/−3 | −22 | −14 | >36 |
| D | 1.0 | −5/−2 | −30 | −27 | >40 |
| E | 1.0 | −13/−14 | −11 | −14 | >36 |
| F | 1.0 | −11/−18 | −23 | −23 | >63 |

2. Effect on the contraction power and frequency of isolated auricles of the guinea pig The maximum delivered tension (isomeric contraction power) and frequency were measured in spontaneously beating, isolated auricles from 4-5 guinea pigs, maintained in a carbogen-bubbled solution at a temperature of 30° C. The tension was registered isometrically on a Grass polygraph. The substances were added to the bath cumulatively in increasing concentrations at intervals of 10 minutes between the individual concentration steps. Because of the poor water solubility, the preparation of the dilutions was started each from 1% solutions in polydiol, which were further diluted in tyrode solutions. The end concentrations of polydiol in the bath of 1:1000 obtained thereby are pharmacologically ineffective.

The following table shows the results:

| Compound | Contraction power | | | | Frequency | | | |
|---|---|---|---|---|---|---|---|---|
| | $10^{-6}$ | $3.10^{-6}$ | $10^{-5}$ | $3.10^{-5}$ | $10^{-6}$ | $3.10^{-6}$ | $10^{-5}$ | $3.10^{-5}$ |
| A | −4.3 | −11.4 | −20.8 | −46.8 | −5.5 | −6.2 | −14.0 | −32.7 |
| B | −4.7 | −9.0 | −27.5 | −49.1 | −3.6 | −12.7 | −28.4 | −53.3 |
| C | −7.5 | −16.5 | −34.6 | −62.6 | −3.5 | −10.2 | −23.6 | −42.5 |
| D | −3.3 | −8.7 | −18.0 | −35.4 | −4.6 | −10.6 | −24.6 | −42.4 |
| E | −3.2 | −9.3 | −16.1 | −30.6 | −3.1 | −6.6 | −17.8 | −28.5 |
| F | −3.0 | −4.4 | −9.4 | −27.3 | −4.1 | −10.5 | −23.3 | −38.6 |

3. Determination of acute toxicity:

The acute toxicity of the test compound was determined in mice (observation period: 14 days) after intravenous administration.

| Compound | Acute toxicity |
|---|---|
| A | >35 mg/kg i.v. (0 out of 5 animals died) |
| B | >35 mg/kg i.v. (0 out of 5 animals died) |
| C | >35 mg/kg i.v. (0 out of 5 animals died) |
| E | >35 mg/kg i.v. (0 out of 5 animals died) |
| F | >35 mg/kg i.v. (0 out of 5 animals died) |

Based on their pharmacological properties the compounds of the invention and their non-toxic, pharmacologically acceptable acid addition salts are especially suitable for the treatment of coronary diseases and hypertension.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. The effective intravenous dosage unit range of the compounds according to the present invention is from 0.28 to 0.71 mgm/kg body weight, and the oral dosage is 0.71 to 3.57 mgm/kg body weight, 2 to 3 times daily.

The following examples illustrate a few pharmaceutical dosage unit compositions comprising a compound of the present invention as an active ingredient and represent the best modes contemplated of using the invention. The parts are parts by weight unless otherwise specified.

EXAMPLE 33

Tablets

The tablet composition is compounded from the following ingredients:

| | |
|---|---|
| 2-[4-(2-Hydroxy-3-tert.butylamino-propoxy)-phenyl]-3-methyl-6-methoxy-3,4-dihydro-quinazoline-4-one | 100.0 parts |
| Lactose | 50.0 parts |
| Polyvinyl pyrrolidone | 5.0 parts |
| Carboxymethyl cellulose | 19.0 parts |
| Magnesium stearate | 1.0 parts |
| Total | 175.0 parts |

Preparation

The active ingredient and the lactose are intimately admixed with each other, the mixture is uniformly moistened with an aqueous solution of the polyvinyl pyrrolidone, and the moist mass is granulated by passing it through a screen. The granulate is dried and then admixed with the remaining ingredients, and the composition is compressed into 175 mgm-tablets. Each tablet is an oral dosage unit composition containing 100 mgm of the active ingredient.

EXAMPLE 34

Suppositories

The suppository composition is compounded from the following ingredients:

| | |
|---|---|
| 2-[4-(2-Hydroxy-3-tert.butylamino-propoxy)-phenyl]-3-methyl-6-methoxy-3,4-dihydro-quinazolin-4-one | 150.0 parts |
| Suppository base (e.g. cocoa butter) | 1550.0 parts |
| Total | 1700.0 parts |

Preparation

The active ingredient is homogeneously blended with the aid of an immersion homogenizer into the suppository base which had previously been melted and cooled to 40° C. 1700 mgm-portions of the composition are poured at 37° C. into cooled suppository molds and allowed to harden therein. Each suppository is a rectal dosage unit composition containing 150 mgm of the active ingredient.

EXAMPLE 35

Coated tablets

The tablet core composition is compounded from the following ingredients:

| | |
|---|---|
| 2-[4-(2-Hydroxy-3-tert.butylamino-propoxy)-phenyl]-3-methyl-6-methoxy-3,4-dihydro-quinazolin-4-one | 50.0 parts |
| Corn starch, dry | 20.0 parts |
| Soluble starch | 2.0 parts |
| Carboxymethyl cellulose | 7.0 parts |
| Magnesium stearate | 1.0 parts |
| Total | 80.0 parts |

Preparation

The ingredients are compounded in a manner analogous to that described in Example 33, and the composition is compressed into 80 mgm-tablet cores which are subsequently coated with a thin shell consisting essentially of an mixture of sugar and talcum. Each coated tablet is an oral dosage unit composition containing 50 mgm of the active ingredient.

EXAMPLE 36
Suspension

The suspension is compounded from the following ingredients:

| | | |
|---|---|---|
| 2-[4-(2-Hydroxy-3-tert.butylamino-propoxy)-phenyl]-3-methyl-6-methoxy-3,4-dihydro-quinazolin-4-one | 5.0 | parts |
| Carboxymethul cellulose | 0.1 | parts |
| Methyl p-hydroxy-benzoate | 0.05 | parts |
| Propyl p-hydroxy-benzoate | 0.01 | parts |
| Sugar | 10.0 | parts |
| Glycerin | 5.0 | parts |
| Sorbitol solution, 70% | 20.0 | parts |
| Flavoring | 0.3 | parts |
| Distilled water q.s.ad | 100.0 | parts by vol. |

Preparation

The p-hydroxy-benzoates, the glycerin and the carboxymethyl cellulose are dissolved in the distilled water at 70° C. while stirring. The solution is cooled to room temperature, and the active ingredient is homogeneously dispersed therein by stirring. After adding the sugar, the sorbitol solution and the flavoring, the resulting suspension is de-aerated by stirring in vacuo. 10 ml of the suspension are an oral dosage unit composition containing 50 mgm of the active ingredient.

Any one of the other compounds embraced by formula I or a non-toxic, pharmacologically acceptable acid addition salt thereof may be substituted for the particular active ingredient in Examples 33 through 36. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

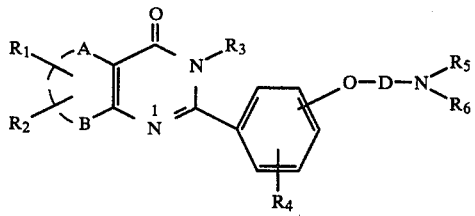

wherein
A and B, together with each other and the respective carbon atoms to which they are attached, form a phenyl or pyridine ring;
$R_1$ is hydrogen, halogen, amino, nitro, alkyl or 1 to 3 carbon atoms or alkoxy of 1 to 3 carbon atoms;
$R_2$ is hydrogen or alkoxy of 1 to 3 carbon atoms;
D is alkylene of 3 to 4 carbon atoms or hydroxy(alkylene of 3 to 4 carbon atoms);
$R_3$ and $R_5$, which may be identical to or different from each other, are each hydrogen or alkyl of 1 to 3 carbon atoms;
$R_4$ is hydrogen or alkoxy of 1 to 3 carbon atoms; and
$R_6$ is straight or branched alkyl of 1 to 6 carbon atoms or —E—$R_7$;
where E is straight alkylene of 2 to 4 carbon atoms or hydroxy-substituted straight alkylene of 2 to 4 carbon atoms, and
$R_7$ is

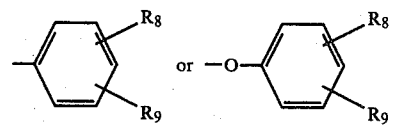

where $R_8$ and $R_9$ are each hydrogen, alkyl of 1 to 3 carbon atoms or alkoxy of 1 to 3 carbon atoms,
or a non-toxic, pharmacologically acceptable acid addition salt thereof.

2. A compound of claim 1,
where A and B, together with each other and the respective carbon atoms to which they are attached, form a phenyl or pyridine ring;
$R_1$ is chlorine, methyl, methoxy or nitro;
$R_2$ is methoxy;
D is n-propylene, n-butylene, 2-hydroxy-n-propylene, 2-hydroxy-n-butylene or 3-hydroxy-n-butylene;
$R_3$ and $R_5$ are each alkyl of 1 to 3 carbon atoms or hydrogen;
$R_4$ is hydrogen or methoxy; and
$R_6$ is alkyl of 4 carbon atoms, 2-(methoxy-phenyl)-ethyl, 2-(dimethoxy-phenyl)-ethyl, 2-(methyl-phenoxy)-ethyl, 2-(methoxy-phenoxy)-ethyl, 2-hydroxy-3-(methoxy-phenoxy)-propyl or 2-hydroxy-3-(methyl-phenoxy)-propyl;
or a non-toxic, pharmacologically acceptable acid addition salt thereof.

3. A compound of claim 1
where A and B, together with each other and the respective carbon atoms to which they are attached and substituents $R_1$ and $R_2$, are phenyl, methoxyphenyl, dimethoxyphenyl or pyridine;
D is n-propylene or 2-hydroxy-n-propylene;
$R_3$ is hydrogen or methyl;
$R_4$ is hydrogen or methoxy;
$R_5$ is hydrogen or alkyl of 1 to 3 carbon atoms; and
$R_6$ is alkyl of 1 to 4 carbon atoms, 2-(methoxy-phenyl)-ethyl, 2-(dimethoxy-phenyl)-ethyl, 2-(methyl-phenoxy)-ethyl, 2-(methoxy-phenoxy)-ethyl, 2-hydroxy-3-(methoxy-phenoxy)-propyl or 2-hydroxy-3-(methyl-phenoxy)-ethyl;
or a non-toxic, pharmacologically acceptable acid addition salt thereof.

4. A compound of claim 1, of the formula

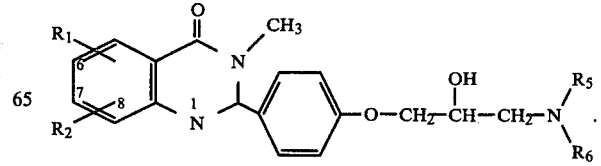

wherein
- R$_1$ is 6- or 8-methoxy;
- R$_2$ is hydrogen or 7-methoxy; and
- R$_5$ and R$_6$, together with the nitrogen atom to which they are attached, are isopropylamino, tert.butylamino, N-methyl-N-[2-(3,4-dimethoxy-phenyl)-ethyl]-amino, 2-(2-methoxy-phenyl)-ethylamino, 2-(2-methyl-phenoxy)-ethylamino or 2-(2-methoxy-phenoxy)-ethylamino;

or non-toxic, pharmacologically acceptable acid addition salt thereof.

5. A compound of claim 1, which is 2-[4-(2-hydroxy-3-tert.-butylamino-propoxy)-phenyl]-3-methyl-6-methoxy-3,4-dihydro-quinazolin-4-one or a non-toxic, pharmacologically acceptable acid addition salt thereof.

6. A compound of claim 1, which is 2-{4-[2-Hydroxy-3-(2-(3,4-dimethoxy-phenyl)-N-methyl-ethylamino)-propoxy]-phenyl}-3-methyl-6-methoxy-3,4-dihydro-quinazolin-4-one or a non-toxic, pharmacologically acceptable acid addition salt thereof.

7. A compound of claim 1, which is 2-{4-[2-Hydroxy-3-(2-(2-methoxy-phenyl)-ethylamino)-propoxy]-phenyl}-3-methyl-6-methoxy-3,4-dihydro-quinazolin-4-one or a non-toxic, pharmacologically acceptable acid addition salt thereof.

8. A pharmaceutical composition consisting essentially of an inert pharmaceutical carrier and an effective hypotensive or antiarrhythmic amount of a compound of claim 1.

9. The method of lowering the blood pressure or alleviating cardiac arrhythmia in a warm-blooded animal in need thereof, which comprises perorally, parenterally or rectally administering to said animal an effective hypotensive or antiarrhythmic amount of a compound of claim 1.

* * * * *

UNITED STATES PATENT AND TRADEMARK OFFICE
CERTIFICATE OF CORRECTION

PATENT NO. : 4,379,788
DATED : April 12, 1983
INVENTOR(S) : JOACHIM HEIDER ET AL.

Page 1 of 2

It is certified that error appears in the above—identified patent and that said Letters Patent is hereby corrected as shown below:

Abstract [57]: Correct the first structural formula to read:

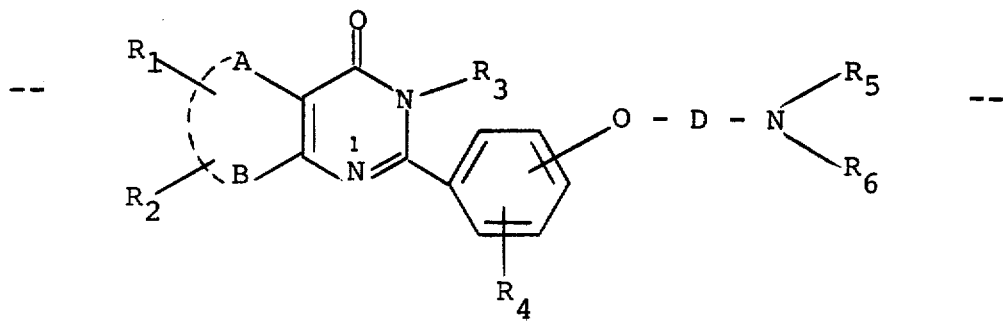

Column 2, line 33; Column 10, line 8: "methox-" should read -- methoxy- --.
Column 2, line 34: "yphenyl" should read -- phenyl --.
Column 7, line 14: "3methyl" should read -- 3-methyl --.
Column 8, line 9: "4one" should read -- 4-one --.
Column 8, line 35: "N-7.15%" should read -- N-7.51% --.
Column 8, line 40: "dimethox-" should read -- dimethoxy- --.
Column 8, line 41: "ybenzylamine" should read -- benzylamine --.

UNITED STATES PATENT AND TRADEMARK OFFICE
CERTIFICATE OF CORRECTION

PATENT NO. : 4,379,788

DATED : April 12, 1983          Page 2 of 2

INVENTOR(S) : JOACHIM HEIDER ET AL.

It is certified that error appears in the above—identified patent and that said Letters Patent is hereby corrected as shown below:

Column 10, line  9: "yphenoxy" should read -- phenoxy --.

Column 16, line 54: "$C_{30}H_{36}ClN_3O_5$" should read -- $C_{30}H_{36}ClN_3O_6$ --.

Column 21, line 66: "or" should read -- of --.

Signed and Sealed this

Twentieth Day of December 1983

[SEAL]

Attest:

Attesting Officer

GERALD J. MOSSINGHOFF

Commissioner of Patents and Trademarks